(12) United States Patent
Aoki (10) Patent No.: US 7,850,833 B2
(45) Date of Patent: Dec. 14, 2010

(54) OXYGEN SENSOR AND AIR/FUEL RATIO CONTROL SYSTEM

(75) Inventor: Keiichiro Aoki, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 873 days.

(21) Appl. No.: 11/665,546

(22) PCT Filed: Apr. 7, 2006

(86) PCT No.: PCT/JP2006/307882

§ 371 (c)(1),
(2), (4) Date: Apr. 17, 2007

(87) PCT Pub. No.: WO2006/109864

PCT Pub. Date: Oct. 19, 2006

(65) Prior Publication Data

US 2007/0261960 A1    Nov. 15, 2007

(30) Foreign Application Priority Data

Apr. 13, 2005 (JP) .............................. 2005-115688

(51) Int. Cl.
*G01N 27/26* (2006.01)
*G01N 27/403* (2006.01)
*G01N 27/406* (2006.01)
*G01N 27/409* (2006.01)
*G01N 27/41* (2006.01)
*G01N 27/419* (2006.01)

(52) U.S. Cl. ...................... 204/428; 204/426; 204/427; 204/429; 123/691; 123/693; 123/697; 123/703; 123/406.23; 123/406.45; 123/406.48; 73/23.32; 60/276; 60/285

(58) Field of Classification Search ................ 204/426, 204/427, 428, 429; 123/691, 693, 697, 703, 123/406.23, 406.45, 406.48; 73/23.32; 60/276, 60/285
See application file for complete search history.

(56) References Cited

U.S. PATENT DOCUMENTS 6,182,498 B1 *  2/2001  Mizutani et al. ........... 73/23.32

(Continued)

FOREIGN PATENT DOCUMENTS

CN            1438412 A       8/2003

(Continued)

*Primary Examiner*—Bruce F Bell
(74) *Attorney, Agent, or Firm*—Oblon, Spivak, McClelland, Maier & Neustadt, L.L.P.

(57) ABSTRACT

An oxygen sensor generating an accurate output concerning low-concentration exhaust gas positioned downstream of a three-way catalyst. The oxygen sensor includes an exhaust gas side electrode exposed to an exhaust gas; a reference gas side electrode exposed to a reference gas serving as a reference for oxygen concentration; and an electrolyte positioned between the exhaust gas side electrode and the reference gas side electrode. Further, a reduction mechanism positioned toward a front surface of the exhaust gas side electrode ensures the ratio of the amount of exhaust gas introduced to the exhaust gas side electrode to the amount of an exhaust gas flow to the outside of the oxygen sensor is smaller than the ratio of the amount of exhaust gas introduced to an electrode for the air-fuel ratio sensor to the amount of an exhaust gas flow to the outside of the air-fuel ratio sensor.

10 Claims, 7 Drawing Sheets

U.S. PATENT DOCUMENTS

| | | | |
|---|---|---|---|
| 2001/0054553 A1* | 12/2001 | Isomura et al. | 204/431 |
| 2002/0060152 A1 | 5/2002 | Hotta et al. | |
| 2002/0102347 A1* | 8/2002 | Clyde et al. | 427/58 |
| 2003/0075440 A1* | 4/2003 | Jain et al. | 204/421 |
| 2003/0209433 A1* | 11/2003 | LaBarge et al. | 204/426 |
| 2004/0117974 A1* | 6/2004 | Clyde et al. | 29/592.1 |
| 2006/0021325 A1* | 2/2006 | Ikemoto et al. | 60/276 |

FOREIGN PATENT DOCUMENTS

| | | |
|---|---|---|
| JP | 7 197837 | 8/1995 |
| JP | 9 189679 | 7/1997 |
| JP | 10 306742 | 11/1998 |
| JP | 11 237361 | 8/1999 |
| JP | 2002 181769 | 6/2002 |
| JP | 2004 301579 | 10/2004 |

* cited by examiner

OXYGEN SENSOR AND AIR/FUEL RATIO CONTROL SYSTEM

TECHNICAL FIELD

The present invention relates to an oxygen sensor and air-fuel ratio control system, and more particularly to an oxygen sensor that is positioned downstream of a catalyst for an internal combustion engine and to an air-fuel ratio control system that includes sensors upstream and downstream of the catalyst for the internal combustion engine and exercises air-fuel ratio control by correcting the output of an air-fuel ratio sensor on the upstream side in accordance with the output of the oxygen sensor on the downstream side.

BACKGROUND ART

A system in which an air-fuel ratio sensor is positioned upstream of a three-way catalyst in an exhaust path for an internal combustion engine is disclosed by Japanese Patent Laid-Open No. 306742/1998. This system calculates an air-fuel ratio control parameter from the output of the air-fuel ratio sensor and uses the calculated parameter to adjust the air-fuel ratio for a target air-fuel ratio.

The output of the air-fuel ratio sensor may be in error because the output characteristic of the air-fuel ratio sensor varies from one unit to another and changes due to sensor aging. If there is an error in the output of the air-fuel ratio sensor on the upstream side in a situation where the control parameter is calculated only from the output of the air-fuel ratio sensor, the error directly affects the control parameter. As a result, air-fuel ratio control accuracy deteriorates.

In the above system, therefore, an exhaust gas sensor is positioned downstream of the three-way catalyst in addition to the air-fuel ratio sensor, which is positioned upstream of the three-way catalyst. This exhaust gas sensor is used to correct the output of the air-fuel ratio sensor on the upstream side. More specifically, a correction value for correcting the output of the air-fuel ratio sensor on the upstream side is calculated in accordance with the output of the sensor on the downstream side. The output of the air-fuel ratio sensor on the upstream side is corrected by the correction value. The control parameter is then calculated from the corrected sensor output. The above system curbs the influence of an error in the air-fuel ratio sensor on the upstream side because such a parameter is used for air-fuel ratio control.

[Patent Document 1]:
Japanese Patent Laid-Open No. 1998-306742
[Patent Document 2]:
Japanese Patent Laid-Open No. 1999-237361

DISCLOSURE OF THE INVENTION

Problem to be Solved by the Invention

An oxygen sensor is generally used as a downstream exhaust gas sensor. The oxygen sensor is characterized so that its output inverts stepwise. More specifically, if the concentration of rich gas such as $CH_4$ and $H_2$ in an exhaust gas is high, the oxygen sensor outputs a predetermined high voltage. If a lean state prevails due to a high oxygen concentration in the exhaust gas, the oxygen sensor's output voltage suddenly drops. A point at which the output voltage suddenly changes is referred to as a sudden output change point. To maintain air-fuel ratio control accuracy, it is preferred that the sudden output change point be in the vicinity of a theoretical air-fuel ratio, that is, a point at which the excess air factor $\lambda=1$.

The exhaust gas contains $CH_4$, $H_2$, and other rich gases and $O_2$. However, $CH_4$ and $H_2$ have a higher diffusion rate than $O_2$. Therefore, when the oxygen sensor is used for exhaust gas detection, $CH_4$ and $H_2$ arrive at the surface of an exhaust gas side electrode earlier than $O_2$. Consequently, even when a theoretical air-fuel ratio prevails, the output of the oxygen sensor may deviate toward the rich side due to the influence of the rich gases that arrive earlier.

Even when the diffusion rates of molecules in the exhaust gas differ from each other as described above, the resulting output remains nearly unaffected and is more or less accurate as far as the molecules in the exhaust gas to be detected have a high concentration. However, the oxygen sensor positioned downstream of the three-way catalyst detects an extremely low concentration gas that is purified by the three-way catalyst. Therefore, the output of the oxygen sensor is likely to be considerably affected by different diffusion rates. Thus, the sudden output change point may readily shift toward the lean side to generate a rich output. When the output of the oxygen sensor on the downstream side deviates from normal as described above, the output of the air-fuel ratio sensor on the upstream side cannot be accurately corrected.

The present invention has been made to solve the above problem. It is an object of the present invention to provide an oxygen sensor and air-fuel ratio control system that are improved to obtain an accurate output from the oxygen sensor, which is positioned downstream of a three-way catalyst.

Means for Solving the Problem

First aspect of the present invention is an oxygen sensor that is positioned downstream of a three-way catalyst for an internal combustion engine, the oxygen sensor comprising:

an exhaust gas side electrode that is exposed to an exhaust gas;

a reference gas side electrode that is exposed to a reference gas, which serves as a reference for oxygen concentration;

an electrolyte that is positioned between the exhaust gas side electrode and the reference gas side electrode; and reduction means that is positioned toward a front surface of the exhaust gas side electrode to reduce the amount of rich gas in the exhaust gas reaching the exhaust gas side electrode so that the output of the oxygen sensor has a sudden output change point at a theoretical air-fuel ratio.

Second aspect of the present invention is the oxygen sensor according to the first aspect, wherein the reduction means is a coating layer that has a porosity of 10% or less and is positioned opposite the electrolyte being in contact with the exhaust gas side electrode.

Third aspect of the present invention is the oxygen sensor according to the first or the second aspect, wherein the reduction means is a coating layer that has a thickness of 300 µm or more and is positioned opposite the electrolyte being in contact with the exhaust gas side electrode.

Fourth aspect of the present invention is the oxygen sensor according to any one of the first to the third aspects, wherein the reduction means is a cover for installing the oxygen sensor in an isolated manner in a piping that is positioned downstream of the three-way catalyst; and wherein the cover has vent holes, which are adjusted so that the exhaust gas flow rate prevailing at the surface of the coating layer is lower than or equal to $\frac{1}{10}$ the exhaust gas flow rate prevailing outside the cover while the internal combustion engine idles after warm-up.

Fifth aspect of the present invention is an air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the oxygen sensor includes an exhaust gas side electrode that is exposed to an exhaust gas;

a reference gas side electrode that is exposed to a reference gas, which serves as a reference for oxygen concentration;

an electrolyte that is positioned between the exhaust gas side electrode and the reference gas side electrode; and reduction means, which is positioned toward a front surface of the exhaust gas side electrode to ensure that the ratio of the amount of exhaust gas introduced to the exhaust gas side electrode to the amount of an exhaust gas flow to the outside of the oxygen sensor is lower than the ratio of the amount of exhaust gas introduced to an electrode for the air-fuel ratio sensor to the amount of an exhaust gas flow to the outside of the air-fuel ratio sensor.

Sixth aspect of the present invention is the air-fuel ratio control system according to the fifth aspect, wherein the reduction means is a coating layer that is positioned opposite the electrolyte being in contact with the exhaust gas side electrode; and wherein the porosity of the coating layer is reduced to decrease the amount of exhaust gas reaching the exhaust gas side electrode.

Seventh aspect of the present invention is the air-fuel ratio control system according to the sixth aspect, wherein the coating layer has a porosity of 10% or less.

Eighth aspect of the present invention is the air-fuel ratio control system according to any one of the fifth to the seventh aspects, wherein the reduction means is a coating layer that is positioned opposite the electrolyte being in contact with the exhaust gas side electrode; and wherein the thickness of the coating layer is increased to decrease the amount of exhaust gas reaching the exhaust gas side electrode.

Ninth aspect of the present invention is the air-fuel ratio control system according to the eighth aspect, wherein the coating layer has a thickness of 300 µm or more.

Tenth aspect of the present invention is the air-fuel ratio control system according to any one of the fifth to the ninth aspects, wherein the reduction means is a cover for installing the oxygen sensor in an isolated manner in a piping that is positioned downstream of the three-way catalyst; and wherein the cover has vent holes, which make adjustments so that the exhaust gas flow rate prevailing at the surface of the coating layer is lower than the exhaust gas flow rate prevailing in the piping.

Eleventh aspect of the present invention is the air-fuel ratio control system according to the tenth aspect, wherein the vent holes ensure that the exhaust gas flow rate prevailing at the surface of the coating layer is lower than or equal to 1/10 the exhaust gas flow rate prevailing outside the cover while the internal combustion engine idles after warm-up.

Twelfth aspect of the present invention is the air-fuel ratio control system according to any one of the fifth to the eleventh aspects, wherein the control means includes:

first judgment means for judging whether the output of the oxygen sensor is higher than or equal to a first voltage;

first target voltage setup means for setting the first voltage as a target voltage when the output of the oxygen sensor is found to be higher than or equal to the first voltage;

second judgment means for judging whether the output of the oxygen sensor is lower than or equal to a second voltage, which is lower than the first voltage, when the output of the oxygen sensor is found to be lower than the first voltage;

second target voltage setup means for setting the second voltage as the target voltage when the output of the oxygen sensor is found to be lower than or equal to the second voltage;

deviation calculation means for determining the deviation between the output of the oxygen sensor and the target voltage; and correction value calculation means for calculating a correction value for the air-fuel ratio sensor from the deviation.

Thirteenth aspect of the present invention is the air-fuel ratio control system according to any one of the fifth to the eleventh aspects, wherein the control means includes:

judgment means for judging whether the output of the oxygen sensor is higher than or equal to a reference voltage;

target voltage setup means for setting a first voltage as a target voltage when the output of the oxygen sensor is found to be higher than or equal to the reference voltage, and setting a second voltage, which is lower than the first voltage, as the target voltage when the output of the oxygen sensor is found to be lower than the reference voltage;

deviation calculation means for determining the deviation between the output of the oxygen sensor and the target voltage; and correction value calculation means for calculating a correction value for the air-fuel ratio sensor from the deviation.

Fourteenth aspect of the present invention is an air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the control means includes:

first judgment means for judging whether the output of the oxygen sensor is higher than or equal to a first voltage;

first target voltage setup means for setting the first voltage as a target voltage when the output of the oxygen sensor is found to be higher than or equal to the first voltage;

second judgment means for judging whether the output of the oxygen sensor is lower than or equal to a second voltage, which is lower than the first voltage, when the output of the oxygen sensor is found to be lower than the first voltage;

second target voltage setup means for setting the second voltage as the target voltage when the output of the oxygen sensor is found to be lower than or equal to the second voltage;

deviation calculation means for determining the deviation between the output of the oxygen sensor and the target voltage; and correction value calculation means for calculating a correction value for the air-fuel ratio sensor from the deviation.

Fifteenth aspect of the present invention is an air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the control means includes:

judgment means for judging whether the output of the oxygen sensor is higher than or equal to a reference voltage;

target voltage setup means for setting a first voltage as a target voltage when the output of the oxygen sensor is found to be higher than or equal to the reference voltage, and setting a second voltage, which is lower than the first voltage, as the target voltage when the output of the oxygen sensor is found to be lower than the reference voltage;

deviation calculation means for determining the deviation between the output of the oxygen sensor and the target voltage; and correction value calculation means for calculating a correction value for the air-fuel ratio sensor from the deviation.

Effects of the Invention

According to the first aspect of the present invention, the front surface of the exhaust gas side electrode has the reduction means, which reduces the amount of rich gas in the exhaust gas reaching the exhaust gas side electrode so that the output of the oxygen sensor has a sudden output change point at the theoretical air-fuel ratio. This makes it possible to average the exhaust gas reaching the exhaust gas side electrode and reduce the influence of a rich gas having a high diffusion rate. Thus, the oxygen sensor according to the first aspect of the present invention provides increased output accuracy.

According to the second aspect of the present invention, the surface of the exhaust gas side electrode has a coating layer having a porosity of not higher than 10% as the reduction means. This makes it possible to average the exhaust gas reaching the exhaust gas side electrode with increased certainty.

According to the third aspect of the present invention, the surface of the exhaust gas side electrode has a coating layer having a thickness of not less than 300 μm as the reduction means. This makes it possible to average the exhaust gas reaching the exhaust gas side electrode with increased certainty.

According to the fourth aspect of the present invention, the cover having vent holes is used as the reduction means. The vent holes are adjusted so that the exhaust gas flow rate prevailing at the surface of the coating layer is not higher than $1/10$ the exhaust gas flow rate prevailing outside the cover. This makes it possible to average the exhaust gas reaching the exhaust gas side electrode with increased certainty.

According to the fifth aspect of the present invention, the output of the air-fuel ratio sensor on the upstream side is corrected in accordance with the output of the oxygen sensor, which is positioned downstream of the three-way catalyst, and the air-fuel ration is controlled in accordance with the corrected output of the air-fuel ratio sensor. The oxygen sensor on the downstream side includes the reduction means, which ensures that the ratio of the amount of exhaust gas introduced to the exhaust gas side electrode to the amount of an exhaust gas flow to the outside of the oxygen sensor is smaller than in the case of the air-fuel ratio sensor on the upstream side. This makes it possible to average the exhaust gas reaching the exhaust gas side electrode of the oxygen sensor and reduce the influence of a rich gas having a high diffusion rate. Thus, an accurate output can be obtained from the oxygen sensor, which detects an extremely low concentration exhaust gas that is positioned downstream of the three-way catalyst. As a result, the output of the air-fuel ratio sensor can be corrected with high accuracy.

According to the sixth to ninth aspects of the present invention, the exhaust gas side electrode surface includes a coating layer as the reduction means. This makes it possible to average the exhaust gas reaching the exhaust gas side electrode with increased certainty.

According to the tenth and eleventh aspects of the present invention, the oxygen sensor cover including the vent holes are used as the reduction means. The vent holes are adjusted before use so as to reduce the exhaust gas flow rate prevailing at the surface of the coating layer. This makes it possible to average the exhaust gas reaching the exhaust gas side electrode with increased certainty.

According to the twelfth aspect of the present invention, the control means sets the first voltage as the target voltage when the oxygen sensor output is higher than the first voltage, sets the second voltage as the target voltage when the oxygen sensor output is not higher than the second voltage, calculates the deviation between the target voltage setting and oxygen sensor output, and calculates the air-fuel ratio sensor correction value from the deviation. In consideration of hysteresis in the output of the oxygen sensor, therefore, it is possible to correct a sensor output deviation that occurs when the air-fuel ratio varies between rich and lean states. Consequently, the output of the oxygen sensor can be obtained with increased accuracy.

According to the thirteenth aspect of the present invention, the control means sets the first voltage as the target voltage when the oxygen sensor output is higher than or equal to the reference voltage, sets the second voltage, which is lower than the first voltage, as the target voltage when the oxygen sensor output is lower than the reference voltage, calculates the deviation between the target voltage setting and oxygen sensor output, and calculates the air-fuel ratio sensor correction value from the deviation. In consideration of hysteresis in the output of the oxygen sensor, therefore, it is possible to correct a sensor output deviation that occurs when the air-fuel ratio varies between rich and lean states. Consequently, the output of the oxygen sensor can be obtained with increased accuracy.

According to the fourteenth aspect of the present invention, the control means sets the first voltage as the target voltage when the oxygen sensor output is higher than or equal to the first voltage, sets the second voltage as the target voltage when the oxygen sensor output is not higher than the second voltage, calculates the deviation between the target voltage setting and oxygen sensor output, and calculates the air-fuel ratio sensor correction value from the deviation. In consideration of hysteresis in the output of the oxygen sensor, therefore, it is possible to correct a sensor output deviation that occurs when the air-fuel ratio varies between rich and lean states. Consequently, the output of the oxygen sensor can be obtained with increased accuracy.

According to the fifteenth aspect of the present invention, the control means sets the first voltage as the target voltage when the oxygen sensor output is higher than or equal to the reference voltage, sets the second voltage, which is lower than the first voltage, as the target voltage when the oxygen sensor output is lower than the reference voltage, calculates the deviation between the target voltage setting and oxygen sensor output, and calculates the air-fuel ratio sensor correction value from the deviation. In consideration of hysteresis in the output of the oxygen sensor, therefore, it is possible to correct a sensor output deviation that occurs when the air-fuel ratio varies between rich and lean states. Consequently, the output of the oxygen sensor can be obtained with increased accuracy.

DESCRIPTION OF NOTATIONS 2 internal combustion engine
4 intake port
6 intake branch pipe
8 fuel injection valve
10 surge tank
12 exhaust port
14 common exhaust manifold
16 three-way catalyst
18 catalytic converter
20 exhaust pipe
22 upstream sensor
24 downstream sensor
30 control apparatus
32 microcomputer
34 input port
36, 38 A/D converter
40 output port
42 drive circuit
50 cover
52 vent hole
54 sensor element
56 catalyst layer
58 coating layer
60 exhaust gas side electrode
62 solid electrolyte layer
64 atmosphere side electrode
66 atmospheric chamber
68 heater

BEST MODE FOR CARRYING OUT THE INVENTION

Embodiments of the present invention will now be described with reference to the accompanying drawings. Like elements in the drawings are designated by like reference numerals and will be described in an abbreviated manner or not repeatedly described.

First Embodiment

Figure 1:
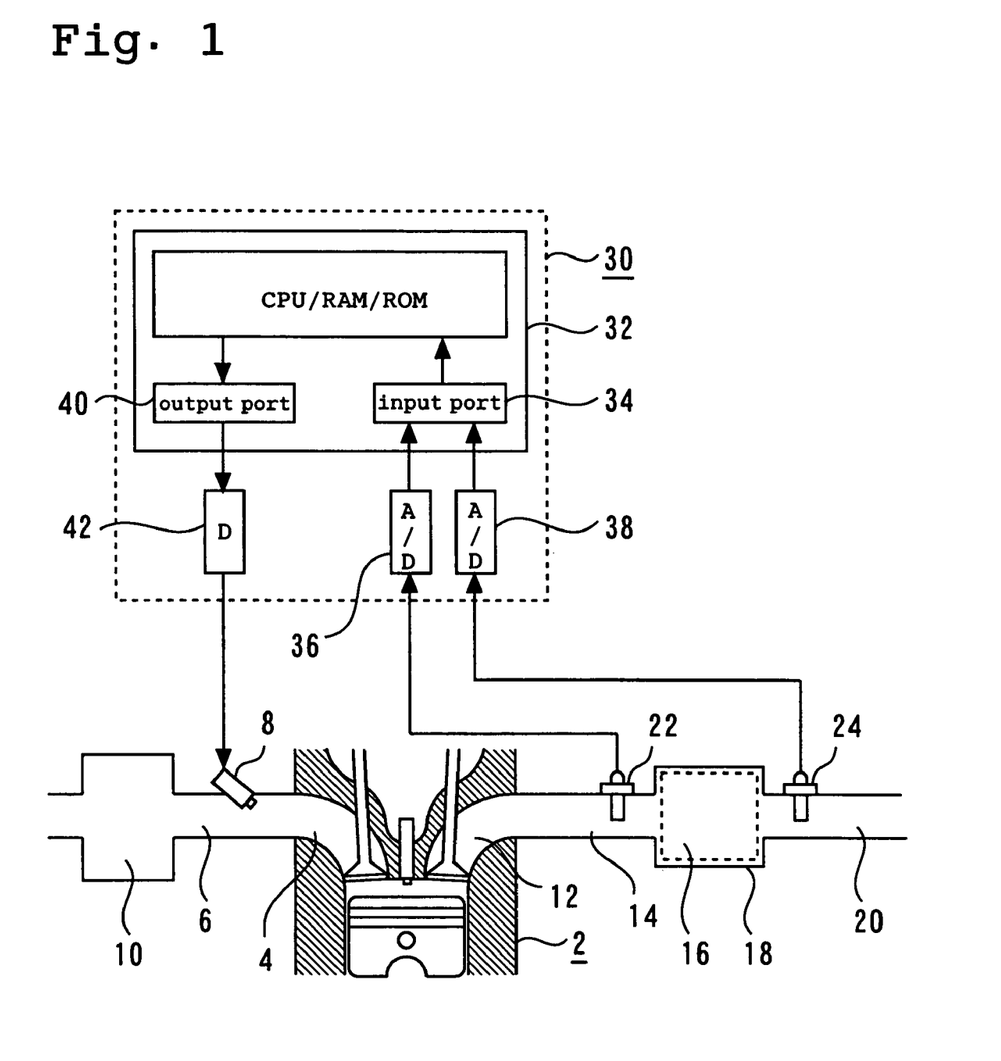
FIG. 1 is a schematic diagram illustrating a system according to a first embodiment of the present invention.

FIG. 1 is a schematic diagram illustrating a system according to a first embodiment of the present invention.

As shown in FIG. 1, the system according to the first embodiment includes an internal combustion engine 2. An intake branch pipe 6 is connected to an intake port 4 for each cylinder in the internal combustion engine 2. The intake branch pipe 6 includes a fuel injection valve 8. The intake branch pipe 6 is also connected to a common surge tank 10.

An exhaust port 12 for each cylinder in the internal combustion engine 2 is connected to a common exhaust manifold 14. The exhaust manifold 14 is connected to a catalytic converter 18 that incorporates a three-way catalyst 16. The catalytic converter 18 is connected to a muffler (not shown) via an exhaust pipe 20. An upstream sensor 22 is positioned upstream of the exhaust manifold 14, that is, upstream of the three-way catalyst 16. The upstream sensor 22 is a so-called wide-region air-fuel ratio sensor, which generates an output voltage according to the air-fuel ratio within a large air-fuel ratio region. Further, a downstream sensor 24 is positioned downstream of the exhaust pipe 20, that is, downstream of the three-way catalyst 16. The downstream sensor 24 is an oxygen sensor whose output value inverts stepwise in the vicinity of a theoretical air-fuel ratio.

The control system described above also includes a control apparatus 30. The control apparatus 30 includes a microcomputer 32. The microcomputer 32 has an input port 34, which is connected to the upstream sensor 22 and downstream sensor 24, respectively, via A/D converters 36, 38. The microcomputer 32 also has an output port 40, which is connected to the fuel injection valve 8 via a drive circuit 42.

Figure 2:
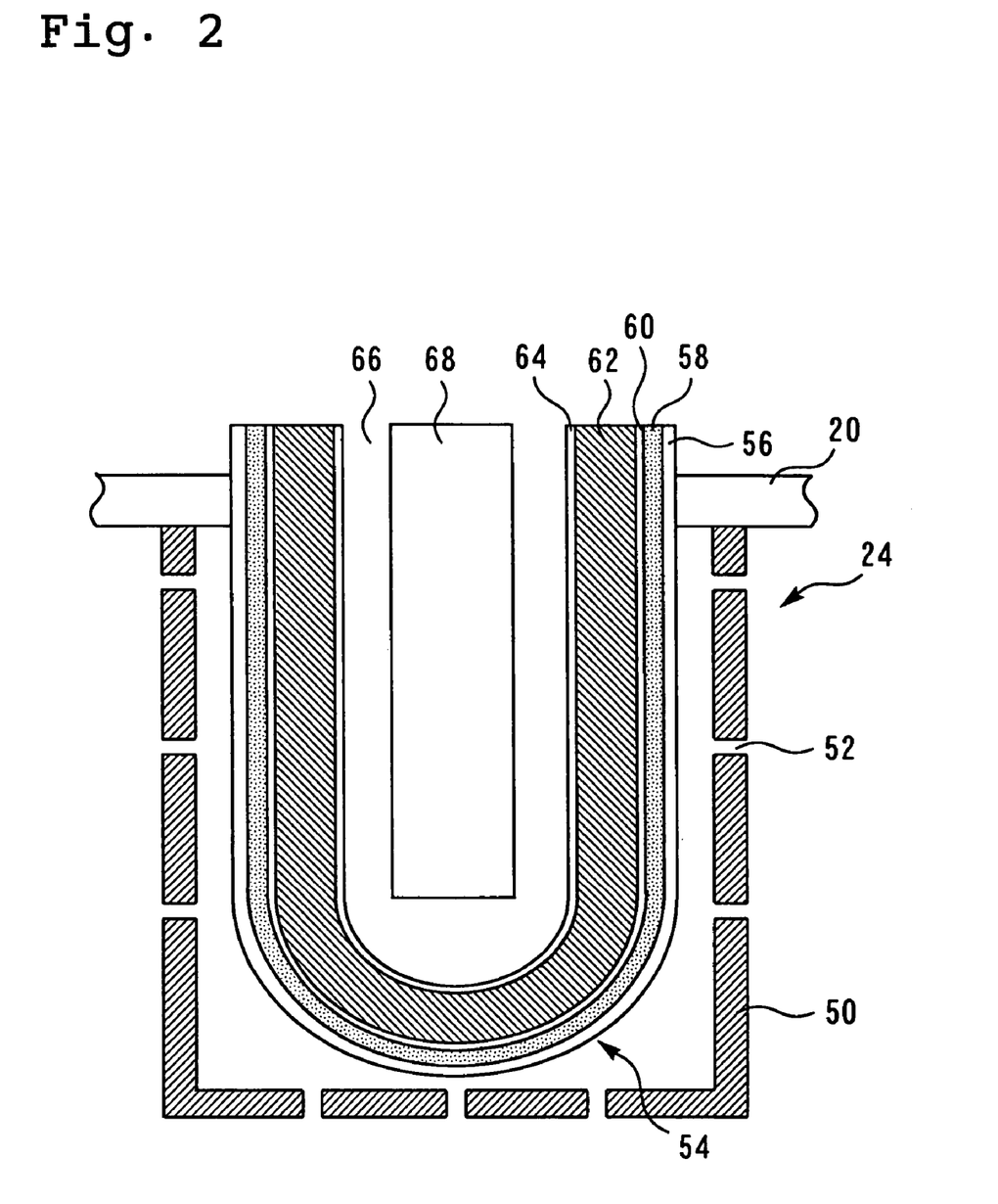
FIG. 2 is a schematic diagram illustrating the downstream sensor that is used in the system according to the first embodiment.

FIG. 2 is a schematic diagram illustrating the downstream sensor 24 that is used in the system according to the first embodiment.

As shown in FIG. 2, the downstream sensor 24 includes a cover 50. The cover 50 is installed in an exhaust gas path within the exhaust pipe 20 and exposed to an exhaust gas. The cover 50 has a plurality of vent holes 52 for introducing the exhaust gas to the inside.

A sensor element 54 is positioned inside the cover 50. The sensor element 54 has a tubular structure, one end of which is closed. The outer surface of the tubular structure is covered with a catalyst layer 56. A coating layer 58 is positioned inside the catalyst layer 56. The coating layer 58 is made of heat-resistant, porous ceramics such as an alumina-based spinel compound ($MgO$—$Al_2O_3$), and governs the exhaust gas diffusion rate prevailing at the surface of the sensor element 54.

An exhaust gas side electrode 60 is positioned inside the coating layer 58. The exhaust gas side electrode 60 is exposed to the exhaust gas that has passed through the coating layer 58. The exhaust gas side electrode 60 is sandwiched between the coating layer 58 and a solid electrolyte layer 62. The solid electrolyte layer 62 is sandwiched between the exhaust gas side electrode 60 and an atmosphere side electrode 64. The exhaust gas side electrode 60 and atmosphere side electrode 64 are made of Pt or other metal that exerts a great catalytic influence.

An atmospheric chamber 66 is formed inside the sensor element 54. The atmospheric chamber 66 is structured so that atmospheric air is introduced into it. Therefore, the atmosphere side electrode 64 is exposed to atmospheric air. A heater 68 is positioned in the atmospheric chamber 66. The heater 68 is electrically connected to a heater control circuit (not shown). The heater control circuit exercises control to heat the sensor element 54 to an appropriate temperature. The sensor element 54 exhibits a stable output characteristic when it is heated to an activation temperature of 700° C. or so.

The upstream sensor 22 has the same structure as a conventional air-fuel ratio sensor. More specifically, the upstream sensor 22 has a diffusion prevention layer instead of the coating layer 58 and catalyst layer 56 for the above-mentioned downstream sensor 24. In the upstream sensor 22, a predetermined voltage is supplied to each electrode.

The coating layer 58 for the downstream sensor 24 is made of a material that is denser than that of the diffusion prevention layer for the upstream sensor 22. More specifically, the coating layer 58 is adjusted for a porosity of 3 to 8%. The porosity is the ratio of space to the volume of the entire coating layer 58 and expressed in space/volume form. Further, the coating layer 58 is thicker than that of a conventional air-fuel ratio sensor and 300 µm in thickness. Thus, the downstream sensor 24 can average the exhaust gas reaching the exhaust gas side electrode 60 in a more gradual manner than the upstream sensor 22.

The vent holes 52 for the downstream sensor 24 have a smaller diameter than the vent holes in the cover for the upstream sensor 22. Further, the number of vent holes 52 for the downstream sensor 24 is smaller than that of vent holes in the cover for the upstream sensor 22. Since the vent holes 52 for the downstream sensor 24 are reduced in diameter and in number, the flow rate of the gas reaching the surface of the sensor element 54 for the downstream sensor 24 is lower than that for the upstream sensor 22. More specifically, setup is performed so that the exhaust gas flow rate prevailing at the surface of the sensor element 54 is not higher than 1/10 the flow rate prevailing in the exhaust pipe 20 when the exhaust gas flows at the lowest rate within a normal engine operation region, that is, when the exhaust gas flows at a rate for idling after warm-up. Therefore, an average exhaust gas can be forwarded to the sensor element 54. When the lowest flow rate prevails, the flow rate prevailing in the exhaust pipe 20 is approximately 1 to 2 m/s and the flow rate prevailing at the surface of the sensor element 54 is approximately 1/10 the flow rate prevailing in the exhaust pipe 20.

Since the employed configuration is as described above, the ratio of the amount of gas reaching the exhaust gas side electrode 60 to the amount of exhaust gas in the exhaust pipe 24 located outside the downstream sensor 24 is smaller than the ratio of the amount of gas reaching the electrode for the upstream sensor 22 to the amount of an exhaust gas in the exhaust manifold 14 located outside the upstream sensor 22. Therefore, the downstream sensor 24 ensures that the gas can be gradually forwarded to the exhaust gas side electrode 60. Thus, an average exhaust gas can be forwarded to the exhaust gas side electrode 60 while the diffusion rate difference between $O_2$ and $H_2$, $CH_4$, or other rich gas is reduced. Further, even if an extremely small amount of rich gas generated by the three-way catalyst 16 mixes with the exhaust gas, the mixture of the rich gas with the exhaust gas can be averaged and forwarded to the exhaust gas side electrode 60. This makes it possible to obtain an accurate sensor output while curbing the influence of a rich gas having a high diffusion rate.

The system according to the first embodiment controls the air-fuel ratio. More specifically, a control parameter is determined from a voltage that is obtained by correcting the output voltage of the upstream sensor 22 in accordance with the output voltage of the downstream sensor 24. A correction value, which is calculated from the output of the downstream sensor 24, is set up through PID control so that the air-fuel ratio obtained from the output of an air-fuel ratio sensor agrees with a target air-fuel ratio. The first embodiment assumes that the target air-fuel ratio is a theoretical air-fuel ratio. In the first embodiment, the control apparatus 30 stores the output of the downstream sensor 24 that prevails when the air-fuel ratio coincides with the theoretical air-fuel ratio, as a target voltage Vref. Air-fuel ratio control provided by the first embodiment will be described in detail below.

Figure 3:
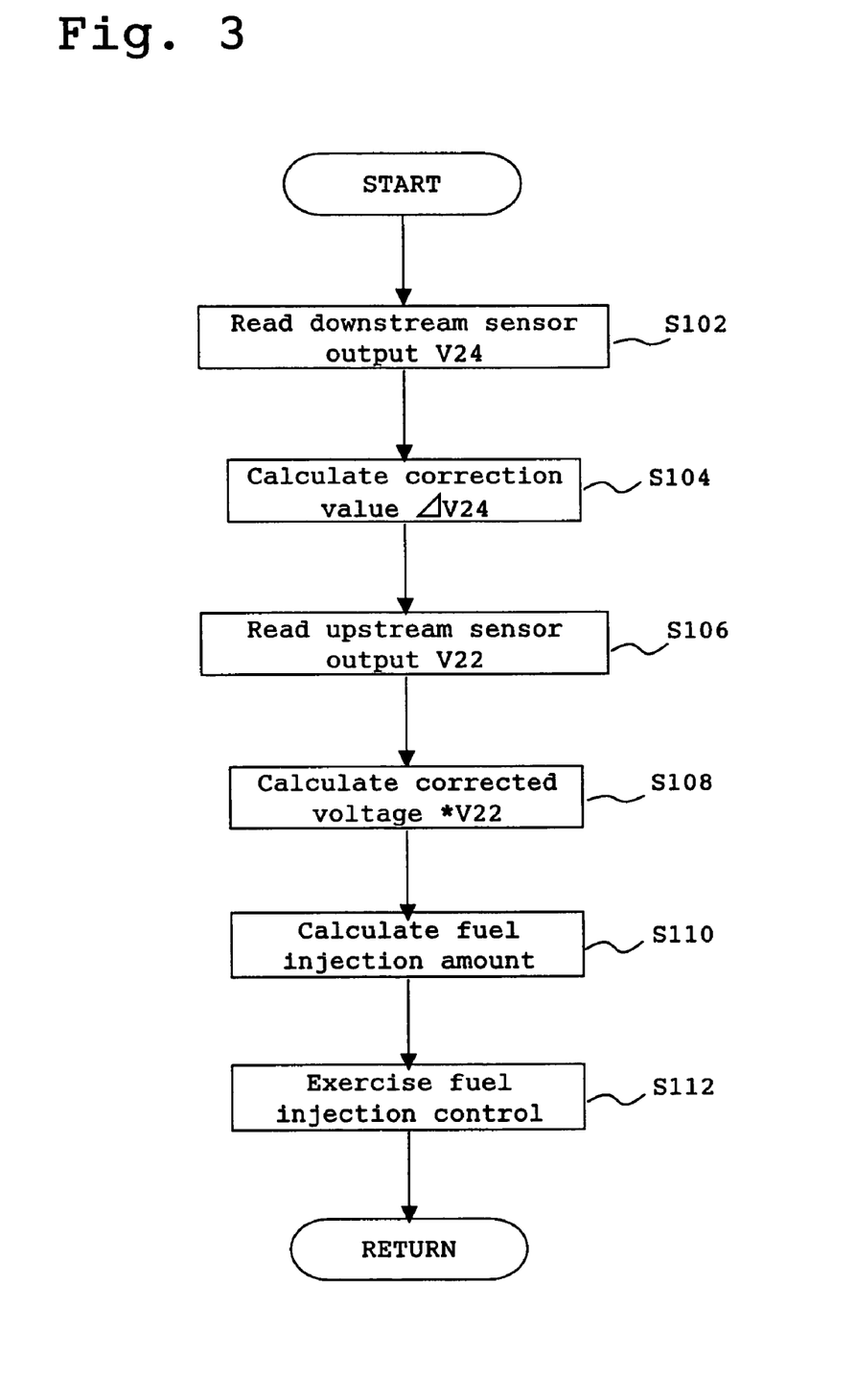
FIG. 3 is a flowchart illustrating a control routine that is executed by the control apparatus in the system according to the first embodiment.

FIG. 3 is a flowchart illustrating a control routine that is executed by the control apparatus 30 in the system according to the first embodiment. As shown in FIG. 3, the control apparatus 30 first reads the output $V_{24}$ of the downstream sensor 24 (step S102). The output of the downstream sensor 24 is forwarded to the A/D converter 38 and then loaded from the input port 34 to the microcomputer 32.

Next, a correction value for the output of the upstream sensor 22 is calculated from the read output $V_{24}$ (step S104). The control apparatus 30 calculates a deviation $\Delta V_{24}$ between the downstream sensor output $V_{24}$ and target voltage Vref, and then calculates the correction value $\Delta V$ from $\Delta V_{24}$ as indicated in Equation (1) below:

$$\Delta V = KP\Delta V_{24} + KI(\Sigma \Delta V_{24}) + KD(d\Delta V_{24}) \quad (1)$$

In Equation (1), $KP\Delta V_{24}$ is a proportional term; $KI(\Sigma \Delta V_{24})$ is an integral term; and $KD(d\Delta V_{24})$ is a derivative term. KP, KI, and KD are gain coefficients for the respective terms. In this correction value, the derivative and proportional terms correct transient changes, and the integral term corrects a steady-state deviation.

Next, the output $V_{22}$ of the upstream sensor 22 is read (step S106). The output $V_{22}$ of the upstream sensor 22 is forwarded to the A/D converter 36 and then loaded from the input port 34 to the microcomputer 32. Subsequently, a corrected voltage $*V_{22}$, which is obtained by correcting the output $V_{22}$ of the upstream sensor 22, is calculated (step S108). The control apparatus 30 calculates the corrected voltage $*V_{22}$ from the output $V_{22}$ of the upstream sensor 22 as indicated in Equation (2) below:

$$*V_{22} = V_{22} + \Delta V \quad (2)$$

The corrected voltage $*V_{22}$ is now based on the correction value $\Delta V$ that is calculated from the output of the downstream sensor 24. In other words, the corrected voltage $*V_{22}$ is obtained after correcting the deterioration with age and output variations of the upstream sensor 22.

Next, the fuel injection amount is calculated (step S110). The fuel injection amount is calculated from the corrected voltage $*V_{22}$. The control apparatus 30 stores, for instance, a calculation method that is based on modern control disclosed by Japanese Patent Laid-Open No. 306742/1998, and uses the stored calculation method to calculate the fuel injection amount.

Next, fuel injection control is exercised in accordance with a preselected fuel injection amount (step S112). The control apparatus 30 controls the fuel injection valve 8 from the output port 40 via the drive circuit 42 so as to inject fuel in accordance with the preselected fuel injection amount. This ensures that the air-fuel ratio is controlled.

The control routine described above is executed for each revolution of a crankshaft. The fuel injection amount for each revolution is constantly PID-controlled in accordance with the outputs of the upstream sensor 22 and downstream sensor 24.

The downstream sensor 24, which is used during the above control operation according to the first embodiment to detect the output $V_{24}$ of the downstream sensor 24, is improved so that the exhaust gas reaching the exhaust gas side electrode 60 can be averaged. Therefore, the influence of a rich gas having a high diffusion rate and the influence of a small amount of rich gas generated from the three-way catalyst can be curbed to obtain a sensor output $V_{24}$ that is based on an averaged gas. Thus, the downstream sensor 24 makes it possible to obtain a highly accurate output while curbing the strong influence of a rich gas. Consequently, the system according to the first embodiment can exercise air-fuel ratio control with high accuracy. The output of the downstream sensor 24 can be used to exercise air-fuel ratio control with high accuracy, for instance, over a small range near the theoretical air-fuel ratio within which the output $V_{24}$ of the downstream sensor 24 varies on a one-to-one basis according to the air-fuel ratio.

The correction value calculation method according to the present invention is not necessarily based on PID control that is described in conjunction with the first embodiment. The present invention also permits the use of another correction value calculation method depending on imposed conditions. For example, the present invention allows the use of a method of using only an annealed value that is obtained by averaging the integral term $KI(\Sigma \Delta V_{24})$ in Equation (1) or a method of calculating the correction value while considering downstream sensor output voltage changes with time for sudden changes between rich and lean states. Even when these alternative methods are used, the air-fuel ratio can be controlled with increased accuracy because the output of the employed downstream sensor 24 is accurate.

The first embodiment assumes that the gas reaching the exhaust gas side electrode 60 is averaged by using four elements, that is, the thickness and porosity of the coating layer 58 and the number and diameter of vent holes 52 in the cover 50. However, the present invention is not limited to the use of such an exhaust gas averaging method. Alternatively, one of the above four elements may be used to adjust the amount of rich exhaust gas reaching the electrode.

The first embodiment assumes that the coating layer 58 is 300 µm in thickness. However, the present invention is not limited to a coating layer thickness of 300 µm. When the function for averaging the exhaust gas and allowing it to reach the exhaust gas electrode 60 is considered, it is preferred that the coating layer 58 be 300 µm or more in thickness. Further, when stability and response of the downstream sensor 24 are considered, it is preferred that the coating layer thickness be not greater than 500 µm. However, the thickness of the coating layer 58 is not limited to the above-mentioned range. The coating layer thickness should be set in consideration of the porosity of the coating layer 58 and the number and diameter of vent holes 52 in the cover 50 so that the exhaust gas is averaged and delivered to the exhaust gas side electrode 60.

The first embodiment assumes that the coating layer 58 has a porosity of 3 to 8%. However, the present invention is not limited to the use of a coating layer having a porosity of 3 to 8%. It is preferred that the coating layer 58 have a porosity of not higher than 10%. However, the porosity of the coating layer 58 is not limited to the above-mentioned range. The coating layer porosity should be set in consideration of the thickness of the coating layer 58 and the number and diameter of vent holes 52 in the cover 50 so that the exhaust gas is averaged and delivered to the exhaust gas side electrode 60.

The first embodiment assumes that the vent holes 52 in the cover 50 have a smaller diameter than in the case of a conventional air-fuel ratio sensor and that the number of vent holes 52 is smaller than that of a conventional air-fuel ratio sensor. The first embodiment also assumes that the exhaust gas flow rate prevailing at the surface of the sensor element 54 is not higher than $\frac{1}{10}$ the flow rate prevailing in the exhaust pipe 20 when the exhaust gas flows at the lowest rate within a normal engine operation region, that is, when the exhaust gas flows at a rate for idling after warm-up. However, the present invention is not limited to the above-mentioned diameter and number of vent holes 52 in the cover 50. The diameter and number of vent holes 52 in the cover 50 should be set in consideration of the thickness and porosity of the coating layer 58 so that the exhaust gas is averaged and delivered to the exhaust gas side electrode 60.

Second Embodiment

Figure 4:
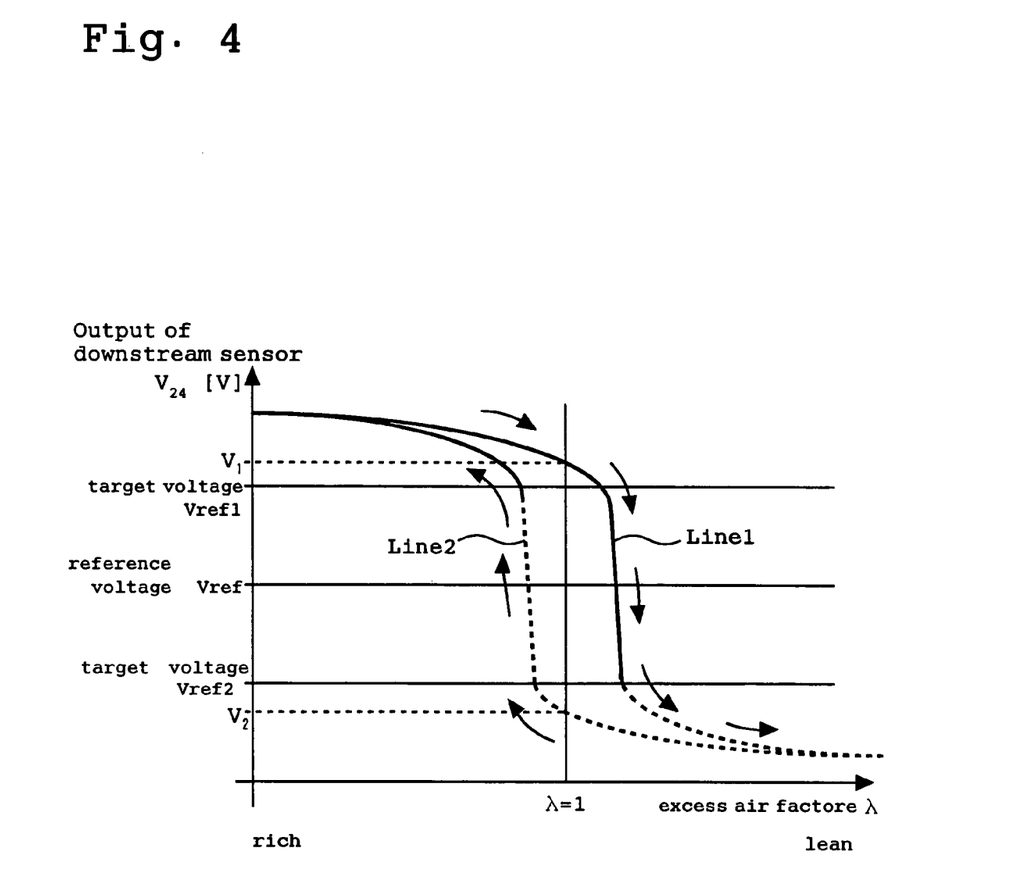
FIG. 4 is a graph illustrating the relationship between the output of the downstream sensor and the two target voltages Vref1, Vref2 in the second embodiment of the present invention.

The system used in the second embodiment is configured the same as the system described in conjunction with the first embodiment. However, the control apparatus 30 stores two target voltages Vref1, Vref2 as the target voltages for calculating a deviation in accordance with the output $V_{24}$ of the downstream sensor 24. FIG. 4 is a graph illustrating the relationship between the output of the downstream sensor 24 in the second embodiment and the two target voltages Vref1, Vref2.

As shown in FIG. 4, hysteresis occurs in the output characteristic of the downstream sensor 24 when the air-fuel ratio changes between rich and lean states in a low-concentration gas atmosphere. In other words, the output generated by the downstream sensor 24 when the air-fuel ratio changes from rich to lean differs from the output generated by the downstream sensor 24 when the air-fuel ratio changes from lean to rich. More specifically, when the air-fuel ratio changes from rich to lean, the sudden output change point of the downstream sensor 24 is shifted toward the lean side. Therefore, the output voltage at the theoretical air-fuel ratio ($\lambda=1$) is shifted to a high-voltage value ($V_1$). On the other hand, when the air-fuel ratio changes from lean to rich, the sudden output change point of the downstream sensor 24 is shifted toward the rich side. Therefore, the output voltage $V_{24}$ at the theoretical air-fuel ratio ($\lambda=1$) is shifted to a low-voltage value ($V_2$).

In consideration of the above-mentioned hysteresis, the second embodiment assumes that when the sensor output $V_{24}$ changes from rich to lean, the target voltage is set at a voltage Vref1 higher than the target voltage (hereinafter referred to as the reference voltage Vref) at the theoretical air-fuel ratio prevailing when no hysteresis is take into account. When, on the other hand, the sensor output $V_{24}$ changes from lean to rich, the second embodiment assumes that the target voltage is set at a voltage Vref2 lower than the reference voltage Vref. The control apparatus 30 stores the target voltages Vref1, Vref2 and selectively uses these target voltages in accordance with changes in the air-fuel ratio. When the target voltage is changed as described above, it is possible to accurately control the sensor output having hysteresis.

Figure 5:
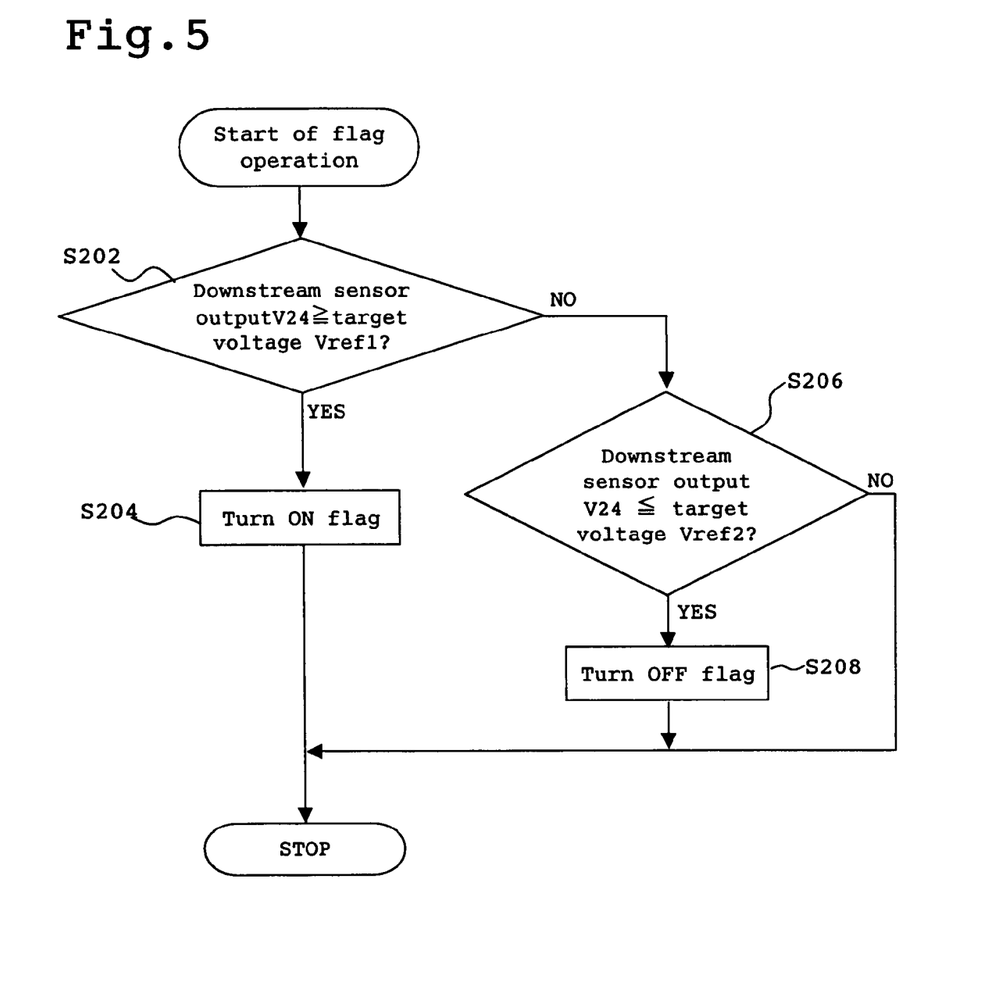
FIG. 5 is a flowchart illustrating a control routine that the control apparatus according to the second embodiment executes to perform flag setup for target voltage setup.
Figure 6:
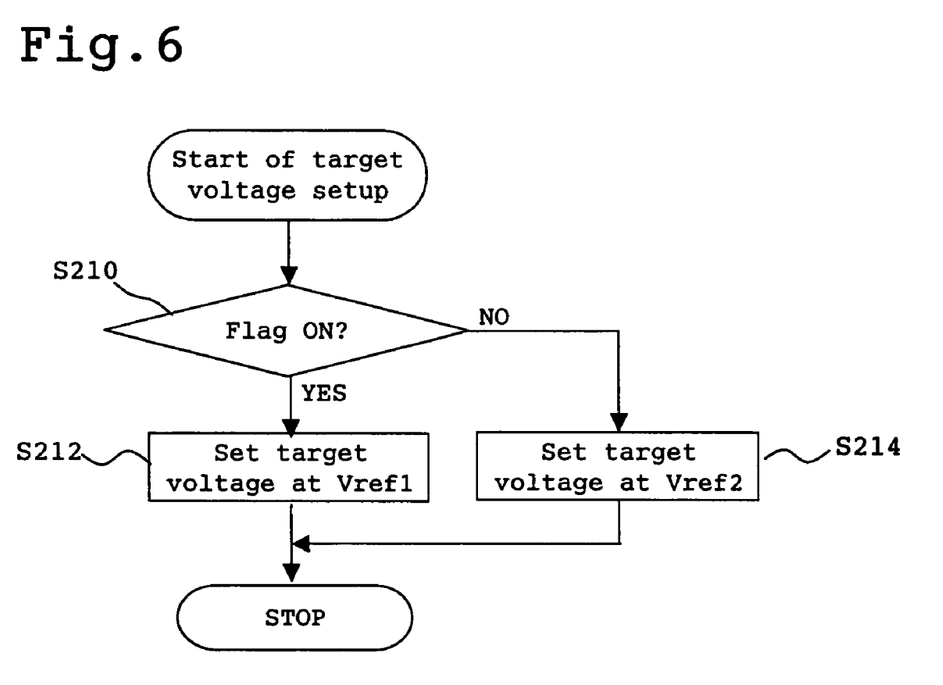
FIG. 6 is a flowchart illustrating a control routine that the control apparatus according to the second embodiment executes to perform target voltage setup.

The control routine executed by the control apparatus 30 is the same as the routine shown in FIG. 3 except that different target voltages are employed. FIG. 5 is a flowchart illustrating a control routine that the control apparatus 30 according to the second embodiment executes to perform flag setup for target voltage setup. This routine is executed after completion of step S102, which is shown in FIG. 3. FIG. 6 is a flowchart illustrating a control routine that the control apparatus 30 according to the second embodiment executes to perform target voltage setup. This routine is executed after completion of the routine shown in FIG. 5.

First of all, control is exercised for flag setup. As shown in FIG. 5, step S202 is performed to judge whether the output voltage $V_{24}$ of the downstream sensor 24, which is read in step S102, is higher than the target voltage Vref1. The control apparatus 30 compares the read output voltage $V_{24}$ against the previously stored target voltage Vref1 to judge whether the output voltage $V_{24}$ is higher than the target voltage Vref1. If the output voltage $V_{24}$ is higher than the target voltage Vref1, the air-fuel ratio changes from rich to lean when control is exercised to restore the air-fuel ratio to the theoretical air-fuel ratio. In other words, step S202 is performed to judge whether the air-fuel ratio output changes from rich to lean when air-fuel ratio control is exercised. If the judgment result obtained in step S202 indicates that the output voltage $V_{24}$ is higher than the target voltage Vref1, step S204 is performed to turn ON a flag and terminate a flag operation routine.

If, on the other hand, the obtained judgment result indicates that the output voltage $V_{24}$ is lower than the target voltage Vref1, step S206 is performed to judge whether the output voltage $V_{24}$ is lower than the target voltage Vref2. The control apparatus 30 compares the output voltage $V_{24}$ against the previously stored target voltage Vref2 to judge whether the output voltage $V_{24}$ is lower than the target voltage Vref2. If the output voltage $V_{24}$ is lower than the target voltage Vref2, the air-fuel ratio changes from lean to rich when control is exercised to restore the air-fuel ratio to the theoretical air-fuel ratio. In other words, step S206 is performed to judge whether the air-fuel ratio output changes from lean to rich when air-fuel ratio control is exercised.

If the judgment result obtained in step S206 indicates that the output voltage $V_{24}$ is higher than the target voltage Vref2, the flag operation routine terminates. If, on the other hand, the judgment result obtained in step S206 indicates that the output voltage $V_{24}$ is lower than the target voltage Vref2, step S208 is performed to turn OFF the flag and terminate the flag operation routine.

When the output voltage $V_{24}$ is higher than the target voltage Vref1, control is exercised as indicated in steps S202 to S208 so that the flag remains ON until the output voltage $V_{24}$ is lower than the target voltage Vref2. When, on the other hand, the output voltage $V_{24}$ is lower than the target voltage Vref2, the flag remains OFF until the output voltage $V_{24}$ is higher than the target voltage Vref1. In other words, the flag is ON in an area that is indicated by a thick solid line portion of line 1, and the flag is OFF in an area that is indicated by a thick broken line portion of line 2.

Next, control is exercised for target voltage setup. First of all, step S210 is performed to judge whether the flag is ON. In other words, step S210 is performed to judge whether control is exercised to change the air-fuel ratio from rich to lean. If the flag is ON, step S212 is performed to set the target voltage for the downstream sensor 24 at Vref1 and terminate a target voltage setup routine. When the flag is ON, it is judged that the air-fuel ratio changes from rich to lean. However, when the air-fuel ratio changes from rich to lean, the sensor output at the theoretical air-fuel ratio is a voltage ($V_1$) higher than the reference voltage Vref. Therefore, the target voltage is set at Vref1, which is higher than the reference voltage Vref.

If, on the other hand, the obtained judgment result does not indicate that the flag is ON, step S214 is performed to set the target voltage for the downstream sensor 24 at Vref2 and terminate the target voltage setup routine. When the flag is OFF, it is judged that the air-fuel ratio changes from lean to rich. However, when the air-fuel ratio changes from lean to rich, the sensor output at the theoretical air-fuel ratio will be a voltage ($V_2$) lower than the reference voltage Vref. Therefore, the target voltage is set at Vref2, which is lower than the reference voltage Vref.

Subsequently, the selected target voltage is used to calculate the correction value as indicated in step S104, which is shown in FIG. 3. Control is then exercised as indicated in steps S106 to S114. This ensures that the air-fuel ratio is PID-controlled.

As described above, the second embodiment determines the target voltage while considering the fact that the output of the downstream sensor 24 has hysteresis. Therefore, the second embodiment can exercise PID control over the air-fuel ratio while the deviation of the output of the downstream sensor 24 is corrected with increased accuracy.

The second embodiment assumes that the target voltages Vref1 and Vref2 are used to judge whether the flag should be turned ON or OFF. However, the present invention is not limited to the use of such judgment values for flag ON/OFF. For example, FIG. 7 shows another example of a control routine for the second embodiment.

Figure 7:
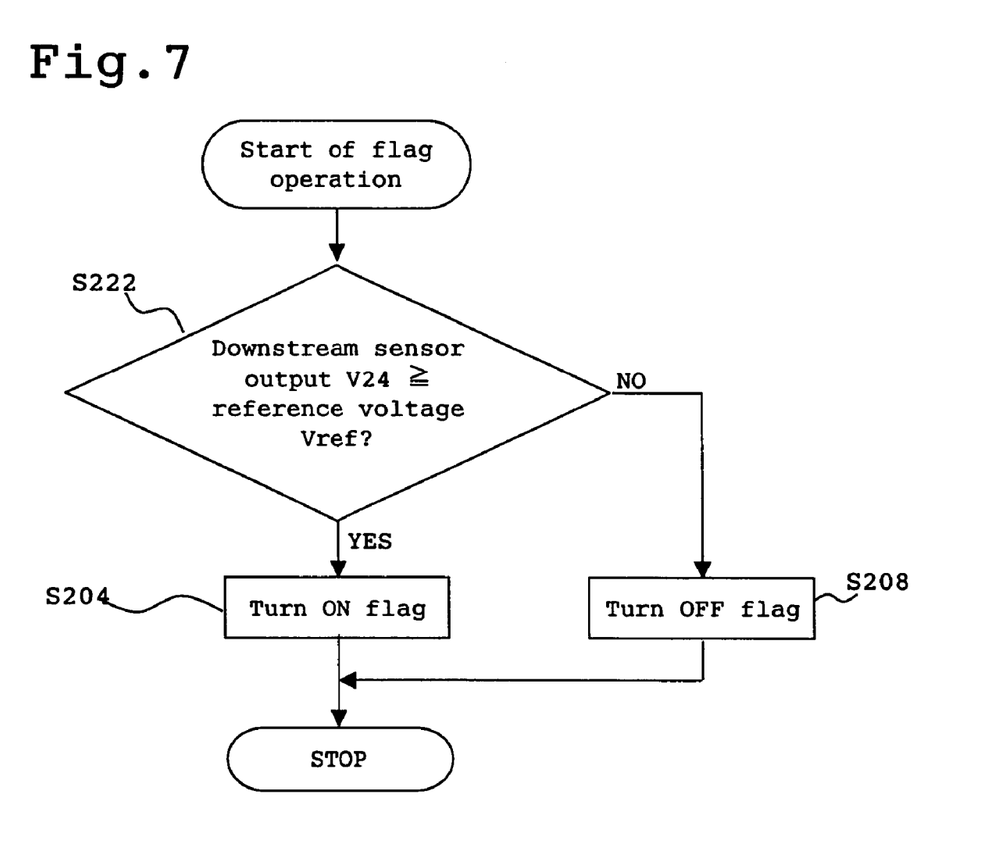
FIG. 7 is a flowchart illustrating another example of a control routine for the second embodiment of the present invention.

The routine shown in FIG. 7 is the same as the routine shown in FIG. 5 except that step S224 is performed in place of steps S204 and S208 of the routine shown in FIG. 5. In the routine shown in FIG. 5, steps S204 and S208 are performed to use Vref1 and Vref2 as judgment values and judge whether $V_{24}$ is greater than Vref1 or smaller than Vref2.

In the routine shown in FIG. 7, on the other hand, step S222 is performed to use the reference voltage Vref as a judgment value and determine whether the flag should be turned ON or OFF. More specifically, step S222 is performed to judge whether the output voltage $V_{24}$ is higher than the reference voltage Vref. If the obtained judgment result indicates that the output voltage $V_{24}$ is higher than the reference voltage Vref, step S204 is performed to turn ON the flag. If, on the other hand, the obtained judgment result does not indicate that the output voltage $V_{24}$ is higher than the reference voltage Vref, step S208 is performed to turn OFF the flag. Subsequently, the routine shown in FIG. 6 is similarly performed in accordance with flag ON/OFF, and an appropriate target voltage is set when the air-fuel ratio changes between rich and lean states.

If, in the routine shown in FIG. 7, the output voltage $V_{24}$ of the downstream sensor 24 is higher than the reference voltage Vref, it is conceivable that a rich state prevails. It is therefore believed that control is exercised to change the air-fuel ratio from rich to lean. Thus, the flag is turned ON to set the target voltage at Vref1. If, on the other hand, the output voltage $V_{24}$ of the downstream sensor 24 is lower than the reference voltage Vref, it is conceivable that a lean state prevails. It is therefore believed that control is exercised to change the air-fuel ratio from lean to rich. Thus, the flag is turned OFF to set the target voltage at Vref2. As described above, target voltage setup can also be performed while using the reference voltage Vref as a reference value for flag ON/OFF judgment.

The second embodiment assumes that the employed downstream sensor 24 is the same as that is used in the first embodiment. However, the present invention is not limited to the use of such a sensor. For example, a conventional oxygen sensor may be used in place of the downstream sensor 24 to provide control as described in conjunction with the second embodiment. The use of such an alternative sensor also makes it possible to provide accurate air-fuel ratio control because the control process described in conjunction with the second embodiment can correct a certain degree of output deviation.

When a numerical value is used to indicate, for instance, the number of elements or the quantity, volume, or range of an element for the purpose of describing the foregoing embodiments, the present invention is not limited to such a numerical value except when the numerical value is used to expressly describe an element or clearly state the principles of an element. Further, structures describing an embodiment and steps followed to implement a method according to an embodiment are not always essential to the present invention except when such structures and steps are used to expressly describe an element or clearly state the principles of an element.

The downstream sensor 24, exhaust gas side electrode 60, atmosphere side electrode 64, and solid electrolyte layer 62 in the first and second embodiments respectively correspond to the "oxygen sensor," "exhaust gas side electrode," "reference gas side electrode," and "electrolyte" according to the present invention. The coating layer 58 and cover 50 in the first and second embodiments respectively correspond to the "coating layer" and "cover" according to the present invention.

In the first embodiment, the "control means" according to the present invention is implemented when the steps S102 to S112 are performed. In the second embodiment, Vref1 and Vref2 respectively correspond to the "first voltage" and "second voltage" according to the present invention; and Vref corresponds to the "reference voltage." Further, referring to FIG. 5 and FIG. 6, the "first judgment means" according to the present invention is implemented when step S202 is performed; the "first target voltage setup means" according to the present invention is implemented when steps S204, S210, and S212 are performed; the "second judgment means" according to the present invention is implemented when step S206 is performed; and the "second target voltage setup means" according to the present invention is implemented when steps S208, S210, and S214 are performed. Furthermore, referring to FIG. 7, the "judgment means" according to the present invention is implemented when step S222 is performed; and the "target voltage setup means" according to the present invention is implemented when steps S204 and S208 are performed.

The invention claimed is:

1. An oxygen sensor that is positioned downstream of a three-way catalyst for an internal combustion engine, the oxygen sensor comprising:
   an exhaust gas side electrode that is exposed to an exhaust gas;
   a reference gas side electrode that is exposed to a reference gas, which serves as a reference for oxygen concentration;
   an electrolyte that is positioned between the exhaust gas side electrode and the reference gas side electrode;
   a coating layer that has a porosity of 10% or less and is positioned opposite the electrolyte being in contact with the exhaust gas side electrode; and
   a cover for installing the oxygen sensor in an isolated manner in a piping that is positioned downstream of the three-way catalyst,
   wherein the cover includes vent holes, which are adjusted so that an exhaust gas flow rate prevailing at the surface of the coating layer is lower than or equal to $1/10$ an exhaust gas flow rate prevailing outside the cover while the internal combustion engine idles after warm-up.

2. An oxygen sensor that is positioned downstream of a three-way catalyst for an internal combustion engine, the oxygen sensor comprising:
   an exhaust gas side electrode that is exposed to an exhaust gas;
   a reference gas side electrode that is exposed to a reference gas, which serves as a reference for oxygen concentration;
   an electrolyte that is positioned between the exhaust gas side electrode and the reference gas side electrode;
   a coating layer that has a thickness of 300 μm or more and is positioned opposite the electrolyte being in contact with the exhaust gas side electrode; and
   a cover for installing the oxygen sensor in an isolated manner in a piping that is positioned downstream of the three-way catalyst,
   wherein the cover includes vent holes, which are adjusted so that an exhaust gas flow rate prevailing at the surface of the coating layer is lower than or equal to $1/10$ an exhaust gas flow rate prevailing outside the cover while the internal combustion engine idles after warm-up.

3. An air-fuel ratio control system comprising:
   an air-fuel ratio sensor that is positioned upstream of a three-way catalyst for purifying an exhaust gas of an internal combustion engine, and used to generate an output in accordance with detected gas concentration;
   an oxygen sensor that is positioned downstream of the three-way catalyst to generate an output in accordance with detected gas concentration; and
   control means for correcting the output of the air-fuel ratio sensor in accordance with the output of the oxygen sensor and providing air-fuel ratio control in accordance with the corrected output of the air-fuel ratio sensor,
   wherein the oxygen sensor includes:
     an exhaust gas side electrode that is exposed to an exhaust gas;
     a reference gas side electrode that is exposed to a reference gas, which serves as a reference for oxygen concentration;
     an electrolyte that is positioned between the exhaust gas side electrode and the reference gas side electrode;
     a coating layer that has a porosity of 10% or less and is positioned opposite the electrolyte being in contact with the exhaust gas side electrode; and
     a cover for installing the oxygen sensor in an isolated manner in a piping that is positioned downstream of the three-way catalyst,
     wherein the cover includes vent holes, which are adjusted so that an exhaust gas flow rate prevailing at the surface of the coating layer is lower than or equal to $1/10$ an exhaust gas flow rate prevailing outside the cover while the internal combustion engine idles after warm-up.

4. The air-fuel ratio control system according to claim 3, wherein the control means includes:
   first judgment means for judging whether the output of the oxygen sensor is higher than or equal to a first voltage;
   first target voltage setup means for setting the first voltage as a target voltage when the output of the oxygen sensor is found to be higher than or equal to the first voltage;
   second judgment means for judging whether the output of the oxygen sensor is lower than or equal to a second voltage, which is lower than the first voltage, when the output of the oxygen sensor is found to be lower than the first voltage;
   second target voltage setup means for setting the second voltage as the target voltage when the output of the oxygen sensor is found to be lower than or equal to the second voltage;
   deviation calculation means for determining the deviation between the output of the oxygen sensor and the target voltage; and
   correction value calculation means for calculating a correction value for the air-fuel ratio sensor from the deviation.

5. The air-fuel ratio control system according to claim 3, wherein the control means includes:
   judgment means for judging whether the output of the oxygen sensor is higher than or equal to a reference voltage;

target voltage setup means for setting a first voltage as a target voltage when the output of the oxygen sensor is found to be higher than or equal to the reference voltage, and setting a second voltage, which is lower than the first voltage, as the target voltage when the output of the oxygen sensor is found to be lower than the reference voltage;

deviation calculation means for determining the deviation between the output of the oxygen sensor and the target voltage; and correction value calculation means for calculating a correction value for the air-fuel ratio sensor from the deviation.

6. An air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the oxygen sensor includes:

an exhaust gas side electrode that is exposed to an exhaust gas;

a reference gas side electrode that is exposed to a reference gas, which serves as a reference for oxygen concentration;

an electrolyte that is positioned between the exhaust gas side electrode and the reference gas side electrode;

a coating layer that has a thickness of 300 μm or more and is positioned opposite the electrolyte being in contact with the exhaust gas side electrode; and a cover for installing the oxygen sensor in an isolated manner in a piping that is positioned downstream of the three-way catalyst, wherein the cover includes vent holes, which are adjusted so that an exhaust gas flow rate prevailing at the surface of the coating layer is lower than or equal to ⅟₁₀ an exhaust gas flow rate prevailing outside the cover while the internal combustion engine idles after warm-up.

7. The air-fuel ratio control system according to claim 6, wherein the control means includes:

first judgment means for judging whether the output of the oxygen sensor is higher than or equal to a first voltage;

first target voltage setup means for setting the first voltage as a target voltage when the output of the oxygen sensor is found to be higher than or equal to the first voltage;

second judgment means for judging whether the output of the oxygen sensor is lower than or equal to a second voltage, which is lower than the first voltage, when the output of the oxygen sensor is found to be lower than the first voltage;

second target voltage setup means for setting the second voltage as the target voltage when the output of the oxygen sensor is found to be lower than or equal to the second voltage;

deviation calculation means for determining the deviation between the output of the oxygen sensor and the target voltage; and correction value calculation means for calculating a correction value for the air-fuel ratio sensor from the deviation.

8. The air-fuel ratio control system according to claim 6, wherein the control means includes:

judgment means for judging whether the output of the oxygen sensor is higher than or equal to a reference voltage;

target voltage setup means for setting a first voltage as a target voltage when the output of the oxygen sensor is found to be higher than or equal to the reference voltage, and setting a second voltage, which is lower than the first voltage, as the target voltage when the output of the oxygen sensor is found to be lower than the reference voltage;

deviation calculation means for determining the deviation between the output of the oxygen sensor and the target voltage; and correction value calculation means for calculating a correction value for the air-fuel ratio sensor from the deviation.

9. An air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the control means includes:

first judgment means for judging whether the output of the oxygen sensor is higher than or equal to a first voltage;

first target voltage setup means for setting the first voltage as a target voltage when the output of the oxygen sensor is found to be higher than or equal to the first voltage;

second judgment means for judging whether the output of the oxygen sensor is lower than or equal to a second voltage, which is lower than the first voltage, when the output of the oxygen sensor is found to be lower than the first voltage;

second target voltage setup means for setting the second voltage as the target voltage when the output of the oxygen sensor is found to be lower than or equal to the second voltage;

deviation calculation means for determining the deviation between the output of the oxygen sensor and the target voltage; and correction value calculation means for calculating a correction value for the air-fuel ratio sensor from the deviation.

10. An air-fuel ratio control system comprising:

an air-fuel ratio sensor that is positioned upstream of a three-way catalyst for purifying an exhaust gas of an internal combustion engine, and used to generate an output in accordance with detected gas concentration;

an oxygen sensor that is positioned downstream of the three-way catalyst to generate an output in accordance with detected gas concentration; and control means for correcting the output of the air-fuel ratio sensor in accordance with the output of the oxygen sensor and providing air-fuel ratio control in accordance with the corrected output of the air-fuel ratio sensor, wherein the control means includes:
  judgment means for judging whether the output of the oxygen sensor is higher than or equal to a reference voltage;
  target voltage setup means for setting a first voltage as a target voltage when the output of the oxygen sensor is found to be higher than or equal to the reference voltage, and setting a second voltage, which is lower than the first voltage, as the target voltage when the output of the oxygen sensor is found to be lower than the reference voltage;
  deviation calculation means for determining the deviation between the output of the oxygen sensor and the target voltage; and
  correction value calculation means for calculating a correction value for the air-fuel ratio sensor from the deviation.

* * * * *